(12) United States Patent
Fujisaki et al.

(10) Patent No.: US 9,414,836 B2
(45) Date of Patent: Aug. 16, 2016

(54) TISSUE LIGATION DEVICE

(71) Applicant: OLYMPUS CORPORATION, Tokyo (JP)

(72) Inventors: Ken Fujisaki, Sagamihara (JP); Takumi Isoda, Tokyo (JP); Hirotaka Namiki, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 66 days.

(21) Appl. No.: 14/140,892

(22) Filed: Dec. 26, 2013

(65) Prior Publication Data

US 2014/0107674 A1  Apr. 17, 2014

Related U.S. Application Data

(63) Continuation of application No. PCT/JP2012/069638, filed on Jul. 26, 2012.

(30) Foreign Application Priority Data

Jul. 27, 2011 (JP) .................................. 2011-164328

(51) Int. Cl.
*A61B 17/12* (2006.01)
*A61B 17/04* (2006.01)
*A61B 17/06* (2006.01)
*A61B 17/062* (2006.01)

(52) U.S. Cl.
CPC .......... *A61B 17/0469* (2013.01); *A61B 17/0401* (2013.01); *A61B 17/12009* (2013.01); *A61B 17/0487* (2013.01); *A61B 17/06* (2013.01); *A61B 17/062* (2013.01)

(58) Field of Classification Search
CPC ........... A61B 17/0401; A61B 17/0469; A61B 17/0487; A61B 17/06; A61B 17/06004; A61B 17/062; A61B 17/12; A61B 17/12009; A61B 2017/0404; A61B 2017/0406; A61B 2017/0409; A61B 2017/0414; A61B 2017/0488; A61B 2017/06019; A61B 2017/06028; A61B 2017/06033; A61B 2017/06057

See application file for complete search history.

(56) References Cited

U.S. PATENT DOCUMENTS

| 3,910,281 A | * | 10/1975 | Kletschka et al. | ............ 606/232 |
| 4,069,825 A | * | 1/1978 | Akiyama | ...................... 606/158 |
| 4,950,285 A | * | 8/1990 | Wilk | .............................. 606/232 |
| 5,037,433 A | * | 8/1991 | Wilk et al. | ..................... 606/139 |

(Continued)

FOREIGN PATENT DOCUMENTS

| JP | 08-140982 A | 6/1996 |
| JP | 3587571 B2 | 11/2004 |

(Continued)

OTHER PUBLICATIONS

International Search Report dated Aug. 28, 2012 issued in PCT/JP2012/069638.

*Primary Examiner* — Ryan J Severson
(74) *Attorney, Agent, or Firm* — Scully, Scott, Murphy & Presser, PC

(57) ABSTRACT

Provided is a tissue ligation device for ligating tissues. The tissue ligation device includes a suture thread, and a hook-like member having a connecting portion connected to a suture thread-side of the connecting portion of the suture thread and a groove whose inner wall has a locking surface disposed so as to face the suture thread-side connecting portion and allowed to be brought into contact with the suture thread.

4 Claims, 19 Drawing Sheets

(56) References Cited

U.S. PATENT DOCUMENTS

| | | | |
|---|---|---|---|
| 5,074,874 A * | 12/1991 | Yoon et al. | 606/224 |
| 5,665,109 A * | 9/1997 | Yoon | 606/232 |
| 5,810,853 A * | 9/1998 | Yoon | 606/151 |
| 5,879,371 A * | 3/1999 | Gardiner et al. | 606/224 |
| 5,972,024 A * | 10/1999 | Northrup et al. | 606/232 |
| 5,984,933 A * | 11/1999 | Yoon | 606/148 |
| 7,862,584 B2 * | 1/2011 | Lyons et al. | 606/232 |
| 8,109,968 B2 * | 2/2012 | Ashley et al. | 606/232 |
| 9,055,939 B2 * | 6/2015 | Fujisaki et al. | |
| 2004/0260344 A1 * | 12/2004 | Lyons et al. | 606/232 |
| 2014/0107674 A1 * | 4/2014 | Fujisaki et al. | 606/148 |
| 2014/0121681 A1 * | 5/2014 | Fujii | 606/144 |

FOREIGN PATENT DOCUMENTS

| | | |
|---|---|---|
| WO | WO 97/25927 A1 | 7/1997 |
| WO | WO 98/30151 A1 | 7/1998 |
| WO | WO 2004/049898 A2 | 6/2004 |

* cited by examiner

TISSUE LIGATION DEVICE

This application is a continuation application based on a PCT Patent Application No. PCT/JP2012/069638, filed on Jul. 26, 2012, whose priority is claimed on Japanese Patent Application No. 2011-164328, filed on Jul. 27, 2011. The contents of both of the PCT Application and the Japanese Application are incorporated herein by reference.

BACKGROUND OF THE INVENTION

1. Technical Field

The present invention relates to a tissue ligation device having a suture thread.

2. Background Art

In the medical field, acts of suturing and ligating tissues occupy a very important position in many procedures. These acts of suturing and ligating tissues are skilled acts. Recently, to reduce the stress of patients, attempts have been made to perform a variety of procedures such as surgery using an endoscope, a laparoscope, or a thoracoscope. In such scope procedures, a suture thread or a suture needle needs to be handled with long forceps. As such, the degree of difficulty for suturing or ligation is further increased.

In the suturing or ligation, it is particularly difficult to bind the suture thread to form a knot.

If the knot is loosened, the suturing or ligation may be released and cause a serious complication.

Depending on the procedure, a plurality of knots may be formed. In this case, the degree of difficulty is further increased.

To solve this problem, a medical suturing device described in Japanese Unexamined Patent Application, First Publication No. H08-140982 is proposed. This medical suturing device includes a suture body in which a suture thread is connected to a thread fastening member. The thread fastening member is formed in a U shape in cross section. The suture thread is formed of a bio-absorbable resin, and a mono-filament (single wire) and a multi-filament (multi wire) can be selectively used as the suture thread.

The suture thread locked in a tissue using a curved needle is drawn into a U-shaped groove of the thread fastening member, and is engaged with the thread fastening member. Thus, a loop is formed by the suture thread. After the suture thread is tightly pulled, when the thread fastening member is deformed by swaging or ultrasonic waves, the suture thread drawn into the U-shaped groove is fixed to the thread fastening member. Thereby, the knot is formed. As such, the knot is easy to form.

SUMMARY OF THE INVENTION

According to a first aspect of the present invention, a tissue ligation device for ligating tissues includes a suture thread, and a hook-like member having a connecting portion connected to a suture thread-side of the connecting portion of the suture thread, and a groove whose inner wall has a locking surface disposed so as to face the suture thread-side connecting portion and allowed to be brought into contact with the suture thread.

According to a second aspect of the present invention, the tissue ligation device according to the first aspect of the present invention may include a direction regulating part that regulates a direction of the suture thread-side connecting portion with respect to the hook-like member.

According to a third aspect of the present invention, in the tissue ligation device according to the first aspect or the second aspect of the present invention, the hook-like member may include a linear part extending linearly from the connecting portion, and a bent part, one end of which is connected to the linear part, and which is curved or flexed on a reference plane including the linear part, thereby providing the groove in which an opening is formed toward the connecting portion.

According to a fourth aspect of the present invention, in the tissue ligation device according to the third aspect of the present invention, the linear part may extend so as to be perpendicular to a reference line that is a central axis of the suture thread-side connecting portion, and the reference plane may be perpendicular to the reference line.

According to a fifth aspect of the present invention, in the tissue ligation device according to the third aspect of the present invention, the linear part may extend so as to be perpendicular to a reference line that is a central axis of the suture thread-side connecting portion, and the reference plane may intersect with the reference line without being perpendicular to the reference line, or include the reference line.

According to a sixth aspect of the present invention, in the tissue ligation device according to the third aspect of the present invention, the linear part may extend so as to move away from the suture thread along a central axis of the suture thread-side connecting portion.

According to a seventh aspect of the present invention, in the tissue ligation device according to the third aspect of the present invention, the linear part may extend toward the suture thread along a central axis of the suture thread-side connecting portion.

According to an eighth aspect of the present invention, in the tissue ligation device according to the third aspect of the present invention, when an orthogonal plane, which is perpendicular to a reference line that is a central axis of the suture thread-side connecting portion and which passes through the suture thread-side connecting portion, is provided, the linear part may extend so as to move away from the suture thread with respect to the orthogonal plane.

According to a ninth aspect of the present invention, in the tissue ligation device according to the third aspect of the present invention, the linear part may extend from an orthogonal plane, which is perpendicular to a reference line that is a central axis of the suture thread-side connecting portion and which passes through the suture thread-side connecting portion, toward the suture thread side.

According to a tenth aspect of the present invention, the tissue ligation device according to any of the first aspect to the ninth aspect of the present invention may include a suture needle connected to the suture thread.

DETAILED DESCRIPTION OF THE INVENTION

First Embodiment

Hereinafter, a tissue ligation device (hereinafter, also called "device") according to a first embodiment of the present invention will be described with reference to FIGS. 1 to 6.

Figure 1:
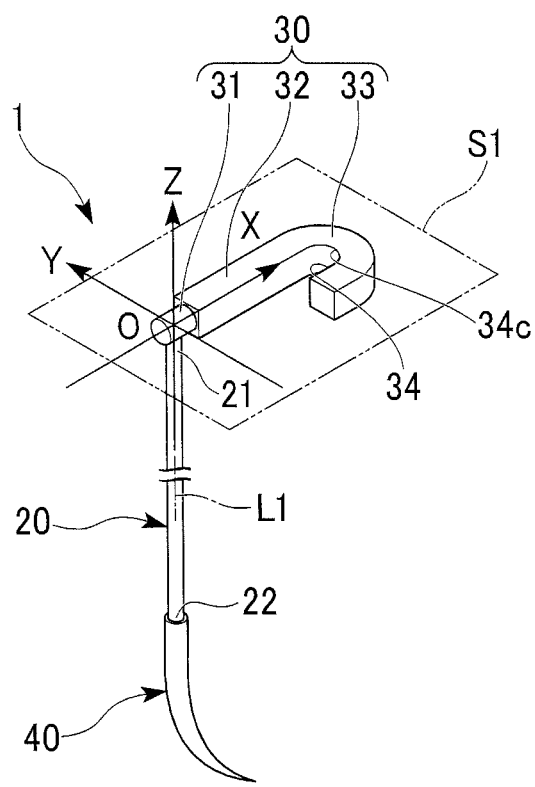
FIG. 1 is a perspective view of a tissue ligation device according to a first embodiment of the present invention.
Figure 2:
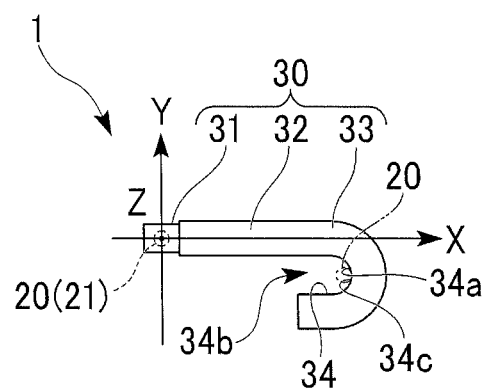
FIG. 2 is a plan view of the tissue ligation device according to the first embodiment of the present invention when viewed in a negative direction of a Z axis.

As shown in FIGS. 1 and 2, a device 1 according to the present embodiment includes a suture thread 20, a hook-like member 30 connected to one end (suture thread-side connecting portion) 21 of the suture thread 20, and a suture needle 40 connected to the other end 22 of the suture thread 20.

In the present first embodiment, the hook-like member 30 is formed of stainless steel.

As a material of which the suture thread 20 and the hook-like member 30 are formed, a metal or a resin may be properly used.

Examples of the metal may include a Co—Cr alloy, β titanium, nickel titanium, pure Ti, a Ti alloy, a Mg alloy, and so on.

On the other hand, the resin that can be used for the suture thread 20 and the hook-like member 30 is classified as an absorbable resin or a non-absorbable resin. The absorbable resin may include polyglycolic acid (PGA), polylactic acid (PLA), polydioxanone (PDS), titanium matrix composite (TMC), poly caprolactone, and a copolymer thereof. The non-absorbable resin may include nylon, polyester, polypropylene, polybutester, fluororesin, and so on.

The hook-like member 30 includes a connecting portion 31 connected to the end 21 of the suture thread 20, a linear part 32 linearly extending from the connecting portion 31, and a curved portion (bent part) 33 connected to the linear part 32 at one end thereof.

Figure 3:
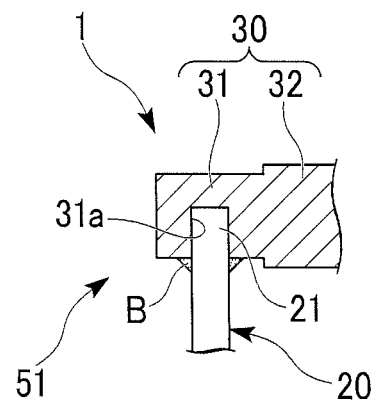
FIG. 3 is a cross-sectional view of important parts of the tissue ligation device according to the first embodiment of the present invention.

As shown in FIG. 3, the connecting portion 31 is provided with a fixing hole 31*a*, an inner diameter of which is set so as to be slightly larger than an outer diameter of the suture thread 20. The end 21 of the suture thread 20 is pressed into the fixing hole 31*a*, and the end 21 and the connecting portion 31 are fixed by an adhesive B. Thereby, the connecting portion 31 is connected to the suture thread 20.

Further, the fixing hole 31*a* and the adhesive B constitute a direction regulating part 51.

Hereinafter, for convenience of description, as shown in FIGS. 1 and 2, the end 21 of the suture thread 20 is set as an origin O, and a central axis at the origin O of the suture thread 20 is defined as a reference line L1.

A Z axis is defined on the reference line L1, and a direction move away from the suture thread 20 is set as a positive direction of the Z axis.

When an orthogonal plane S1 perpendicular to the reference line L1 past the origin O is defined, a right-handed rectangular coordinate system is defined by an X axis and a Y axis that are provided on the orthogonal plane S1 and the Z axis mentioned above.

In the rectangular coordinate system XYZ defined in this way, the linear part 32 extends in a positive direction of the X axis, i.e. so as to be perpendicular to the reference line L1.

The linear part 32 is formed in the shape of a rod extending in one direction.

The curved portion 33 is bent on a reference plane serving as an XY plane, and is provided with a groove 34 on an inner side of the bent. The XY plane on which the hook-like member 30 is disposed is perpendicular to the reference line L1. A central angle of a curved portion at the curved portion 33 is set to about 180 degrees.

The groove 34 is formed so as to pass through the curved portion 33 in a Z direction. A depth of the groove 34 (distance from a bottom 34*a* to an opening 34*b* of the groove 34) and a width of the groove 34 are set so as to be greater than the outer diameter of the suture thread 20 (see FIG. 2). The groove 34 is formed so that the opening 34*b* is directed toward the connecting portion 31, i.e. in a negative direction of the X axis. An inner wall of the groove 34 is provided with a locking surface 34*c*, which is disposed so as to face the end 21 of the suture thread 20 and is allowed to be brought into contact with the suture thread 20. In the curved portion 33, a portion that is an end in the negative direction of the X axis and that is an end in the positive direction of the Y axis is connected to the linear part 32.

The curved portion 33 is connected to an end of the linear part 32 which is opposite to the other end to which the connecting portion 31 is connected.

In the present first embodiment, the connecting portion 31, the linear part 32, and the curved portion 33 are integrally formed by bending a wire made of stainless steel. The hook-like member 30 is formed so as to be harder than the suture thread 20, and may be swaged to undergo plastic deformation.

The linear part 32 and the curved portion 33 are formed so that a cross-sectional shape caused by a plane perpendicular to the direction in which each of them extends is a rectangular shape.

The hook-like member 30 is formed in very small size of, for instance, 10 mm or less.

The suture needle 40 may be appropriately selected from a variety of well-known needles such as a linear needle, a curved needle, a needle that is curved only at a tip thereof and is formed linearly at the other portion thereof, and so on in consideration of a suture region. An aspect of connecting the suture thread 20 and the suture needle 40 is not particularly restricted. Specifically, a method such as adhering, welding, or binding the end of the suture thread 20 into the hole formed in the end of the suture needle 40 may be set forth.

Next, an operation in use of the device 1 configured as described above will be explained taking a case in which tissues of both sides of an opening are sutured by way of example.

Figure 4:
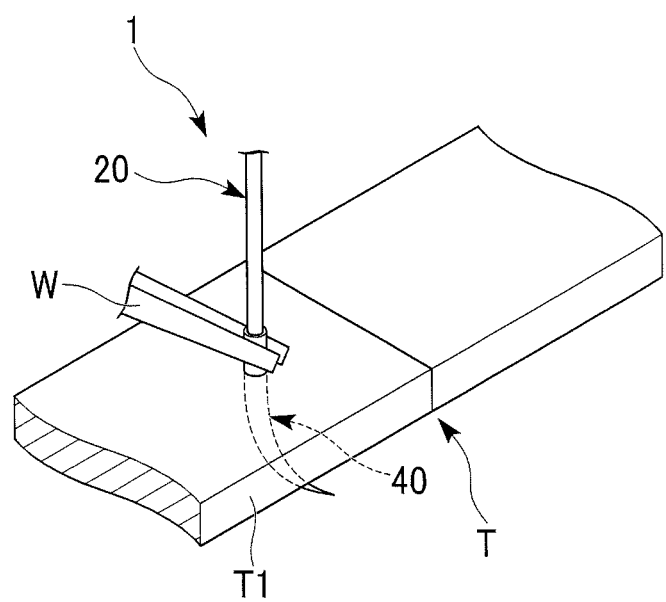
FIG. 4 is an explanatory view showing an operation of stitching tissues using the tissue ligation device according to the first embodiment of the present invention.

First, as shown in FIG. 4, an operator grips the suture needle 40 of the device 1 with grasping forceps W, and punctures the suture needle 40 at a position adjacent to one tissue T1 of an opening T.

Figure 5:
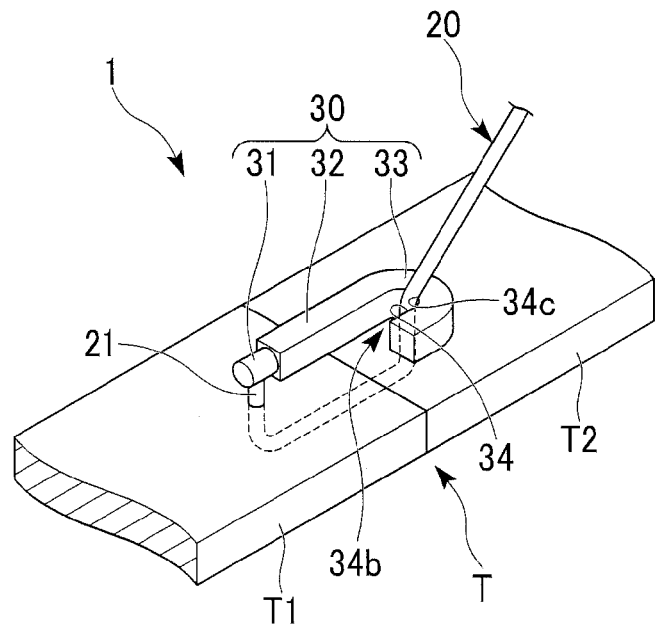
FIG. 5 is an explanatory view showing an operation of stitching tissues using the tissue ligation device according to the first embodiment of the present invention.

As shown in FIG. 5, the suture needle 40 and the suture thread 20 are also threaded through the other tissue T2 of the opening T. The suture needle 40 is pulled so as to move away from the opening T. Thereby, the hook-like member 30 is adjusted so as to be disposed on the tissues T1 and T2. Since the device 1 has the direction regulating part 51, a direction of the hook-like member 30 is stabilized with respect to the suture thread 20.

The grasping forceps W grasping the suture needle 40 is displaced toward the hook-like member 30, and the suture thread 20 is engaged with the groove 34 through the opening 34*b*. Thus, a loop is formed by the suture thread 20. The suture thread 20 is kept engaged with the hook-like member 30, and the suture needle 40 is pulled so as to move away from the end 21 of the suture thread 20. Since the suture thread 20 is brought into contact with the locking surface 34*c* of the hook-like member 30, the suture thread 20 is prevented from disengaging from the hook-like member 30.

Figure 6:
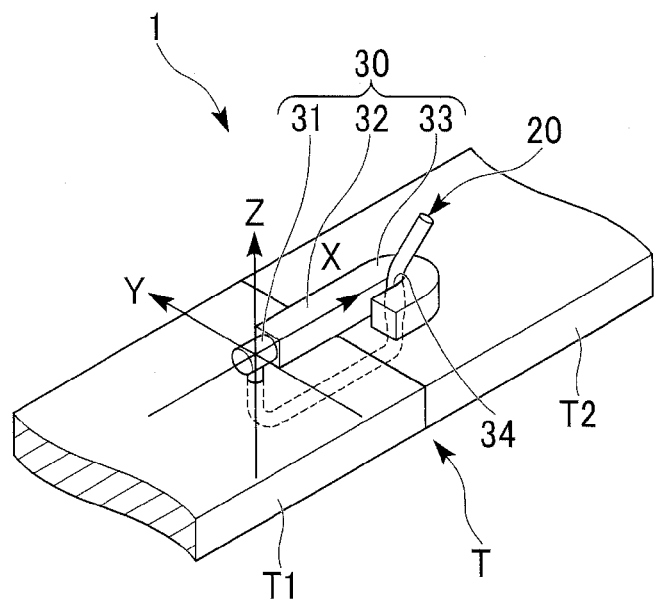
FIG. 6 is an explanatory view showing an operation of stitching tissues using the tissue ligation device according to the first embodiment of the present invention.

Since the direction of the hook-like member 30 with respect to the suture thread 20 is set by the direction regulating part 51, as shown in FIG. 6, the hook-like member 30 is brought into contact with the tissues T1 and T2 in a state in which surfaces of the tissues T1 and T2 are approximately parallel to the XY plane on which the hook-like member 30 is disposed. The suture thread 20 moves in the groove 34 in the Z-axial direction, and the tissues T1 and T2 are constricted by the suture thread 20.

In a state in which the suture needle 40 is pulled so as to move away from the end 21 of the suture thread 20, the curved portion 33 of the hook-like member 30 is swaged so as to be crushed from the outside by another grasping forceps (not shown), and thus the hook-like member 30 is fixed to the suture thread 20. In this manner, a knot is formed by the suture thread 20 and the swaged hook-like member 30, thereby ligating the opening T.

The suture thread 20 is cut with a medical knife or medical scissors on the side of the suture needle 40 rather than the swaged hook-like member 30, and the suture needle 40 and the cut suture thread 20 are drawn out. Thereby, the procedure is terminated.

As described above, according to the device 1 of the present first embodiment, the suture thread 20 is threaded through the tissues T1 and T2, and is engaged with the groove 34 of the hook-like member 30. The suture needle 40 is pulled so as to move away from the end 21 of the suture thread 20.

The groove 34 is open in the Z direction, and the suture thread 20 is guided so as to pass through the opening 34b. Thereby, the suture thread 20 can be easily engaged with the groove 34. Since the suture thread 20 is brought into contact with the locking surface 34c of the hook-like member 30, the suture thread 20 intended to move away from the end 21 is supported by the locking surface 34c, and the suture thread 20 is prevented from disengaging from the hook-like member 30. Accordingly, an operator can easily form the loop of the suture thread 20 with one hand.

Since the device 1 has the direction regulating part 51, the direction of the hook-like member 30 with respect to the suture thread 20 is fixed, and the operator can easily recognize the direction of the hook-like member 30. Thereby, the suture thread 20 can be more simply engaged with the groove 34 of the hook-like member 30.

Since the hook-like member 30 is made up of the linear part 32 and the curved portion 33, the hook-like member 30 can be easily configured. Since the opening 34b is directed toward the connecting portion 31, the operator can easily recognize the direction of the opening 34b.

Further, the XY plane on which the hook-like member 30 is disposed is perpendicular to the reference line L1. Thereby, when the suture thread 20 is threaded through the tissue T1, and the suture needle 40 is pulled to bring the hook-like member 30 into contact with the tissue T1, the surface of the tissue T1 becomes approximately parallel to the hook-like member 30. As such, when the hook-like member 30 is brought into contact with the tissue T1, the tissue T1 can be prevented from being damaged.

Since the device 1 has the suture needle 40, the suture thread 20 connected to the suture needle 40 can easily pass through the tissues T1 and T2.

Second Embodiment

Next, a second embodiment of the present invention will be described with reference to FIGS. 7 to 13. However, the same portions as the first embodiment are assigned the same symbols, and a description thereof will be omitted here, and thus will be made regarding differences only.

Figure 7:
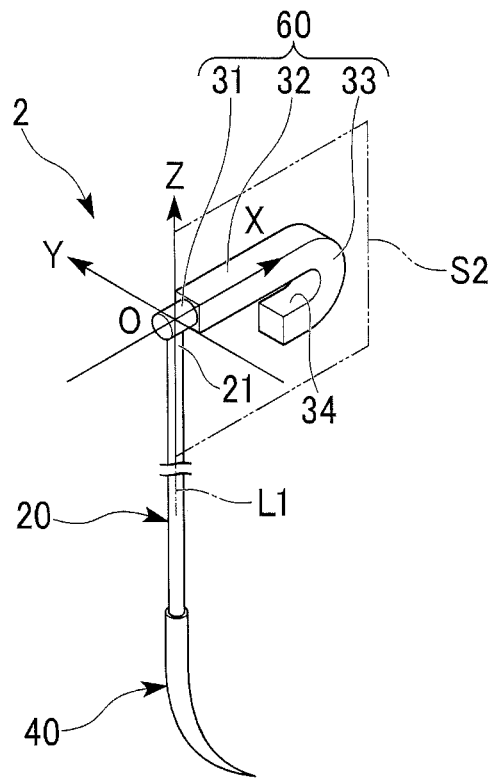
FIG. 7 is a perspective view of a tissue ligation device according to a second embodiment of the present invention.
Figure 8:
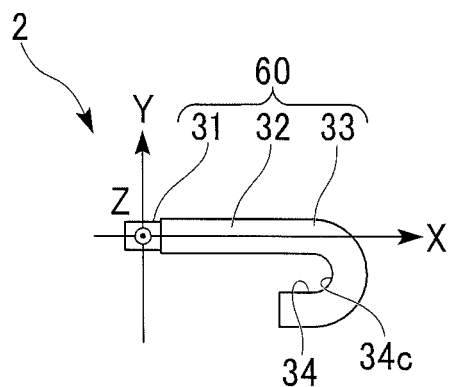
FIG. 8 is a plan view of the tissue ligation device according to the second embodiment of the present invention when viewed in the negative direction of the Z axis.

As shown in FIGS. 7 and 8, a device 2 of the present second embodiment includes a hook-like member 60 in place of the hook-like member 30 of the device 1 of the first embodiment.

The hook-like member 60 is different from the hook-like member 30 in terms of a direction in which a curved portion 33 is connected to a linear part 32. The curved portion 33 is curved on a reference plane S2 that is a ZX plane. The ZX plane on which the curved portion 33 is curved serves as a plane including a reference line L1. A groove 34 is formed so as to pass through the curved portion 33 in the Y direction.

In the curved portion 33, a portion that is an end in the negative direction of the X axis and that is an end in the positive direction of the Z axis is connected to the linear part 32.

Next, an operation in use of the device 2 configured according to the present second embodiment will be described.

Figure 9:
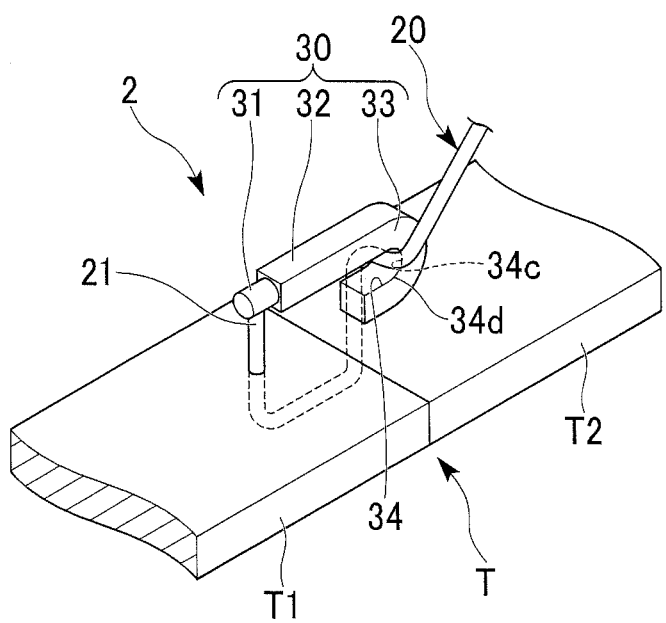
FIG. 9 is an explanatory view showing an operation of stitching tissues using the tissue ligation device according to the second embodiment of the present invention.

As shown in FIG. 9, a suture thread 20 is threaded through tissues T1 and T2, and is engaged with the groove 34 of the hook-like member 60, and a suture needle 40 is pulled so as to move away from an end 21 of the suture thread 20. In this case, since the suture thread 20 is in contact with a locking surface 34c of the hook-like member 60, the suture thread 20 is prevented from disengaging from the hook-like member 60. Since a direction in which the suture thread 20 protrudes from the tissue T2 intersects with a direction in which the groove 34 is open, an angle 34d of an inner wall of the groove 34 gets into the suture thread 20 passing through the inside of the groove 34.

The following operation is similar to the case in which the device 1 is used, and a description thereof will be omitted here.

As described above, according to the device 2 of the present second embodiment, an operator can easily form a loop of the suture thread 20 with one hand.

Furthermore, the reference plane S2 on which the curved portion 33 is curved becomes the plane including the reference line L1. For this reason, after the suture thread 20 is threaded through the tissues T1 and T2, when the suture thread 20 passes through the inside of the groove 34, and when the suture needle 40 is pulled so as to move away from the end 21 of the suture thread 20, the angle 34d of the groove 34 gets into the suture thread 20. Accordingly, it can be made difficult for the suture thread 20 to escape from the groove 34.

The device 2 of the present second embodiment may be variously deformed in shape as will be described below.

Figure 10:
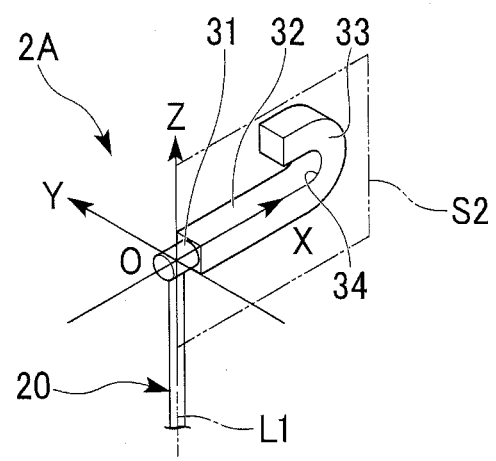
FIG. 10 is a perspective view of important parts of the tissue ligation device in a first modified example of the second embodiment of the present invention.

For a first modified example, as in a device 2A shown in FIG. 10, the curved portion 33 of the device 2 of the present second embodiment may be configured so that a portion that is an end in the negative direction of the X axis and that is an end in the negative direction of the Z axis is connected to the linear part 32.

Even in this case, a reference plane S2 on which the curved portion 33 is curved also becomes a plane including a reference line L1.

Further, in the present second embodiment and in the first modified example, the reference plane S2 on which the curved portion 33 is curved has been described to be the ZX plane including the reference line L1. However, the reference plane on which the curved portion 33 is curved may be a plane that intersects with the reference line L1 without being perpendicular to the reference line L1.

Figure 11:
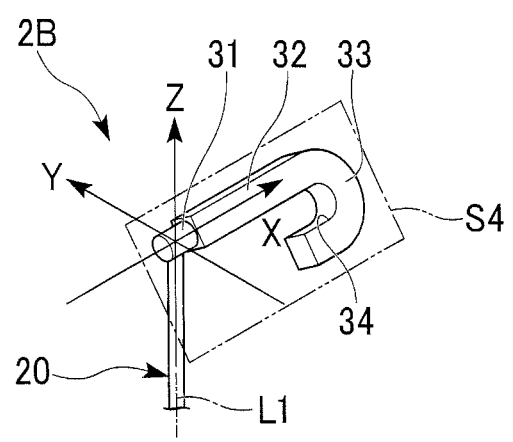
FIG. 11 is a perspective view of important parts of the tissue ligation device in a second modified example of the second embodiment of the present invention.
Figure 12:
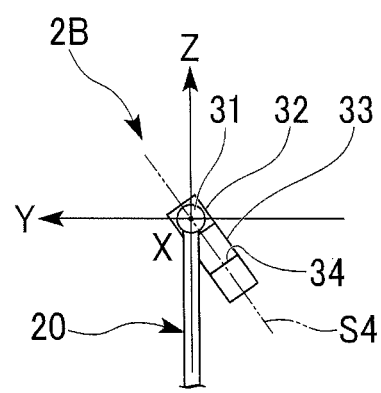
FIG. 12 is a front view of important parts of the tissue ligation device in the second modified example of the second embodiment of the present invention when viewed in a positive direction of an X axis.

For a second modified example, as in a device 2B shown in FIGS. 11 and 12, the curved portion 33 of the device 2 may be configured so as to be disposed on a reference plane S4. The reference plane S4 is a plane that includes the X axis and that passes through an area that is in the positive direction of the Y axis and in the positive direction of the Z axis and an area that is in the negative direction of the Y axis and in the negative direction of the Z axis.

Figure 13:
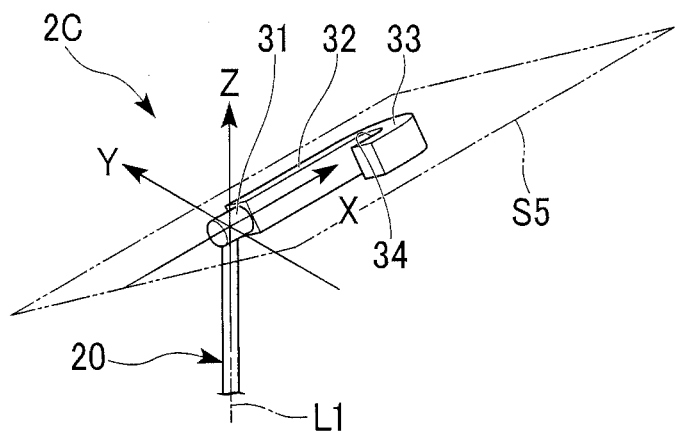
FIG. 13 is a perspective view of important parts of the tissue ligation device in a third modified example of the second embodiment of the present invention.

As in a device 2C according to a third modified example shown in FIG. 13, the curved portion 33 may be configured so as to be disposed on a reference plane S5. The reference plane S5 is a plane that includes the X axis and that passes through an area that is in the positive direction of the Y axis and in the negative direction of the Z axis and an area that is in the negative direction of the Y axis and in the positive direction of the Z axis.

Even by the device 2A, 2B or 2C configured in this way, similar to the device 2 of the present embodiment, it can be made difficult for the suture thread 20 guided to the groove 34 to escape from the groove 34.

Third Embodiment

Next, a third embodiment of the present invention will be described with reference to FIGS. 14 to 16. However, the same regions as in the aforementioned embodiments are assigned the same symbols, and a description thereof will be omitted here, and thus will be made regarding differences only.

Figure 14:
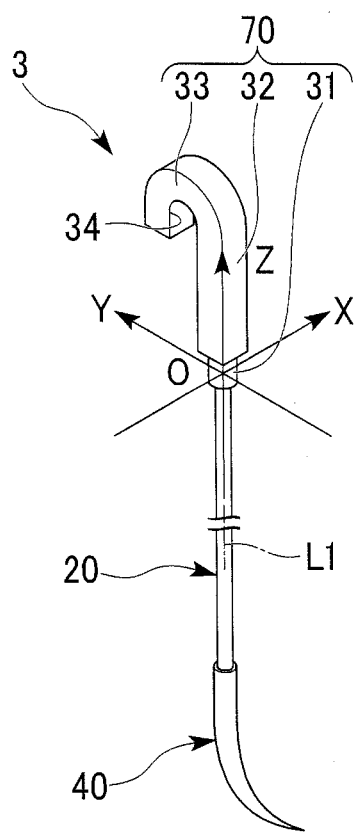
FIG. 14 is a perspective view of a tissue ligation device according to a third embodiment of the present invention.
Figure 15:
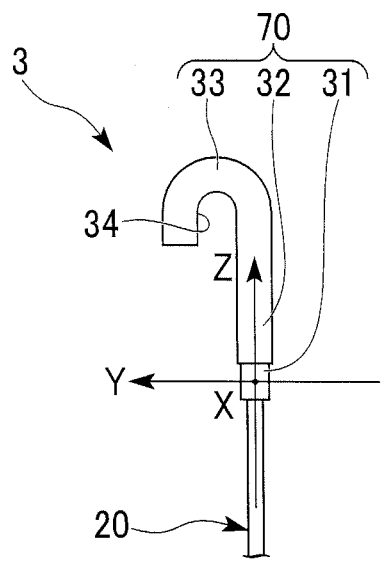
FIG. 15 is a side view of important parts of the tissue ligation device according to the third embodiment of the present invention when viewed in a positive direction of a Y axis.

As shown in FIGS. 14 and 15, a device 3 of the present third embodiment includes a hook-like member 70 in place of the hook-like member 30 of the device 1 of the first embodiment.

The hook-like member 70 is different from the hook-like member 30 in terms of a direction in which a linear part 32 extends from a connecting portion 31.

The linear part 32 extends from the connecting portion 31 toward the side on which it moves away from the suture thread 20 in the positive direction of the Z axis, i.e. along a reference line L1.

In the third embodiment, a plane on which a curved portion 33 is curved is a ZY plane.

Next, an operation in use of the device 3 configured according to the present third embodiment will be described.

The suture thread 20 is threaded through tissues T1 and T2, and a suture needle 40 is pulled so as to move away from an opening T.

Figure 16:
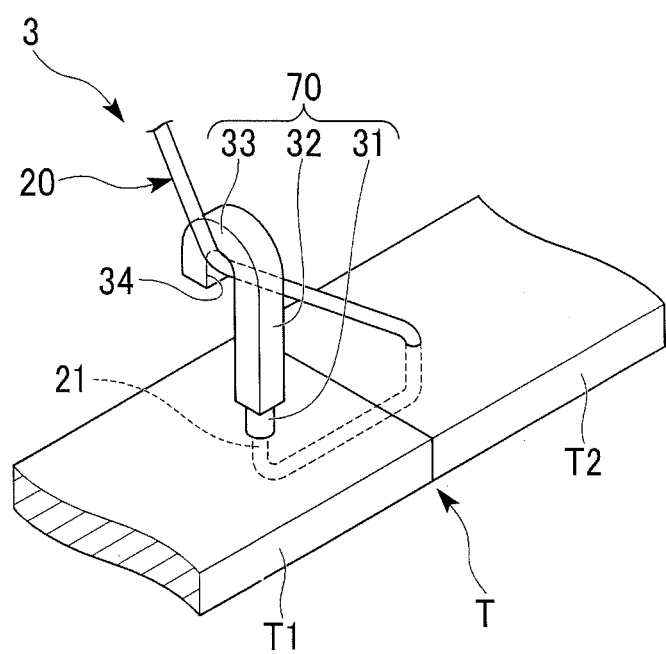
FIG. 16 is an explanatory view showing an operation of stitching tissues using the tissue ligation device according to the third embodiment of the present invention.

When the hook-like member 70 is brought into contact with the tissue T1, the curved portion 33 of the hook-like member 70, as shown in FIG. 16, is kept located above (moved away from) the tissue T1.

The suture thread 20 is engaged with the groove 34 of the hook-like member 70, and the suture needle 40 is pulled so as to move away from an end 21 of the suture thread 20.

The following operation is similar to the case of using the device 1, and a description thereof will be omitted here.

As described above, according to the device 3 of the present third embodiment, an operator can easily form a loop of the suture thread 20 with one hand.

Furthermore, the suture thread 20 threaded through the tissue T1 is pulled. Thereby, when the hook-like member 70 is brought into contact with the tissue T1 (when the suture thread 20 is completely pulled), the curved portion 33 is kept located above the tissue T1. Accordingly, the suture thread 20 can be easily engaged with the groove 34 of the hook-like member 70.

When the suture thread 20 is repetitively threaded through the tissues, the suture thread 20 needs to be completely pulled in order to constrict the tissues to some extent. By using the device 3 of the present third embodiment, for example, even when the suture thread 20 is continuously threaded through the tissues of a tube shape in a circumferential direction, the suture thread 20 can be easily engaged with the curved portion 33 located above the tissue.

Fourth Embodiment

Next, a fourth embodiment of the present invention will be described with reference to FIGS. 17 to 20. However, the same portions as in the aforementioned embodiments are assigned the same symbols, and a description thereof will be omitted here, and thus will be made regarding differences only.

Figure 17:
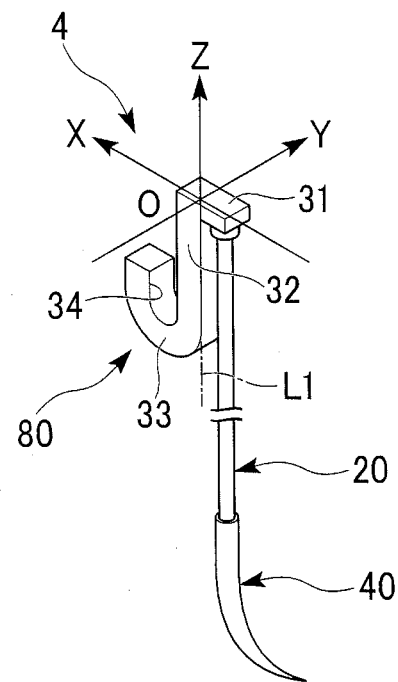
FIG. 17 is a perspective view of a tissue ligation device according to a fourth embodiment of the present invention.
Figure 18:
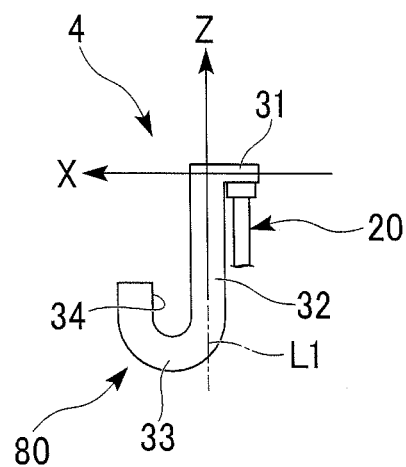
FIG. 18 is a side view of important parts of the tissue ligation device according to the fourth embodiment of the present invention when viewed in a positive direction of a Y axis.

As shown in FIGS. 17 and 18, a device 4 of the present fourth embodiment includes a hook-like member 80 in place of the hook-like member 30 of the device 1 of the first embodiment.

The hook-like member 80 is different from the hook-like member 30 in terms of a direction in which a linear part 32 extends from a connecting portion 31.

The linear part 32 extends from the connecting portion 31 toward a suture thread 20 in the negative direction of the Z axis, i.e. along a reference line L1.

In this example, a plane on which a curved portion 33 is curved is a ZX plane.

Next, an operation in use of the device 4 configured according to the present fourth embodiment will be described.

The suture thread 20 is threaded through tissues T1 and T2, and a suture needle 40 is pulled so as to move away from an opening T.

Figure 19:
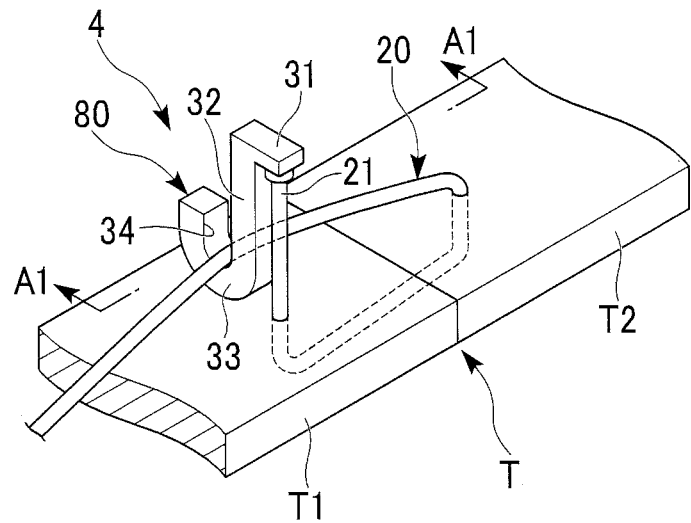
FIG. 19 is an explanatory view showing an operation of stitching tissues using the tissue ligation device according to the fourth embodiment of the present invention.
Figure 20:
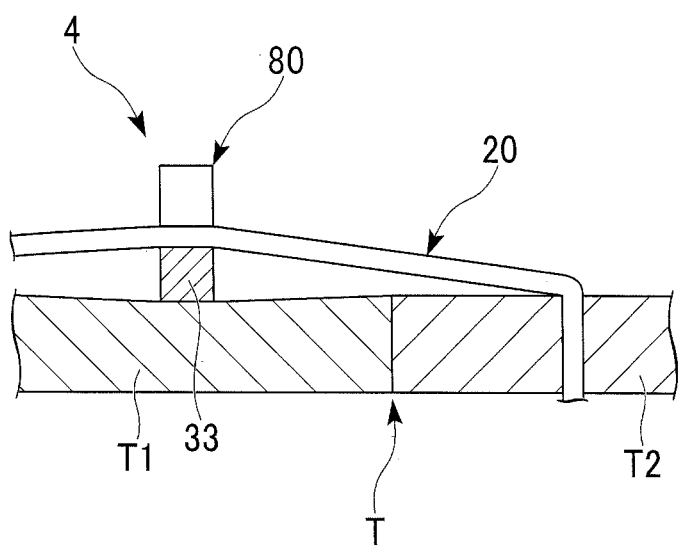
FIG. 20 is a cross-sectional view taken along a cutting line A1-A1 of FIG. 19.

As shown in FIGS. 19 and 20, after the hook-like member 80 is brought into contact with the tissue T1, the suture thread 20 is engaged with a groove 34 of the hook-like member 80, and is displaced (tightly pulled) so as to move away from an end 21. Then, the suture thread 20 is kept tightened, and the curved portion 33 of the hook-like member 80 gets into the tissue T1.

In this state, the curved portion 33 is swaged, and the hook-like member 80 is fixed to the suture thread 20.

As described above, according to the device 4 of the present fourth embodiment, an operator can easily form a loop of the suture thread 20 with on hand.

Furthermore, by causing the hook-like member 80 to get into the tissue T1, the suture thread 20 is prevented from being loosened by elasticity of the tissue T1, and thus the tissues T1 and T2 can be constricted by the suture thread 20.

Fifth Embodiment

Next, a fifth embodiment of the present invention will be described with reference to FIGS. 21 to 25. However, the same portions as in the aforementioned embodiments are assigned the same symbols, and a description thereof will be omitted here, and thus will be made regarding differences only.

Figure 21:
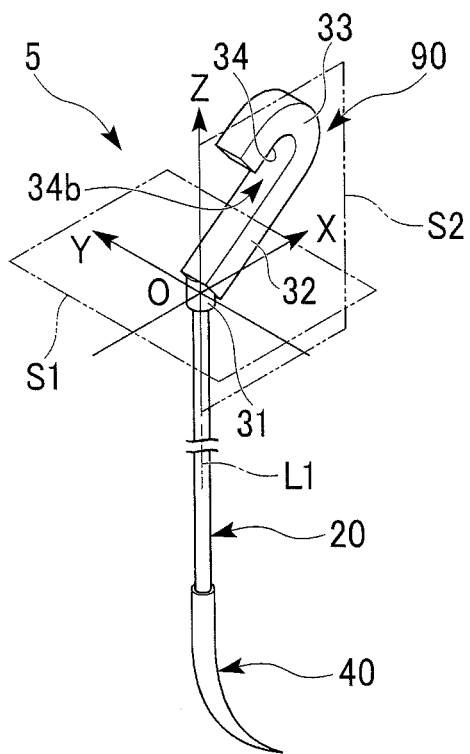
FIG. 21 is a perspective view of a tissue ligation device according to a fifth embodiment of the present invention.
Figure 22:
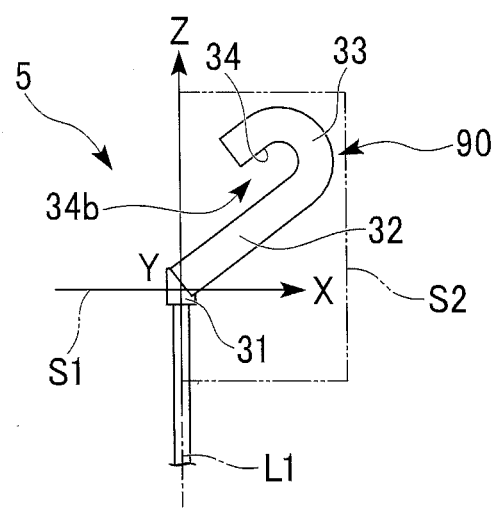
FIG. 22 is a side view of important parts of the tissue ligation device according to the fifth embodiment of the present invention when viewed in the positive direction of the Y axis.

As shown in FIGS. 21 and 22, a device 5 of the present fifth embodiment includes a hook-like member 90 in place of the hook-like member 30 of the device 1 of the first embodiment.

The hook-like member 90 is different from the hook-like member 30 in terms of a direction in which a linear part 32 extends from a connecting portion 31.

The linear part 32 extends from the connecting portion 31 in a direction between the positive direction of the X axis and the positive direction of the Z axis.

A curved portion 33 is curved on the aforementioned reference plane S2 that is a ZX plane. In the curved portion 33, an end in the negative direction of the Z axis is connected to the linear part 32.

Next, an operation in use of the device 5 configured according to the present fifth embodiment will be described.

The suture thread 20 is threaded through tissues T1 and T2, and a suture needle 40 is pulled so as to move away from an opening T.

Figure 23:
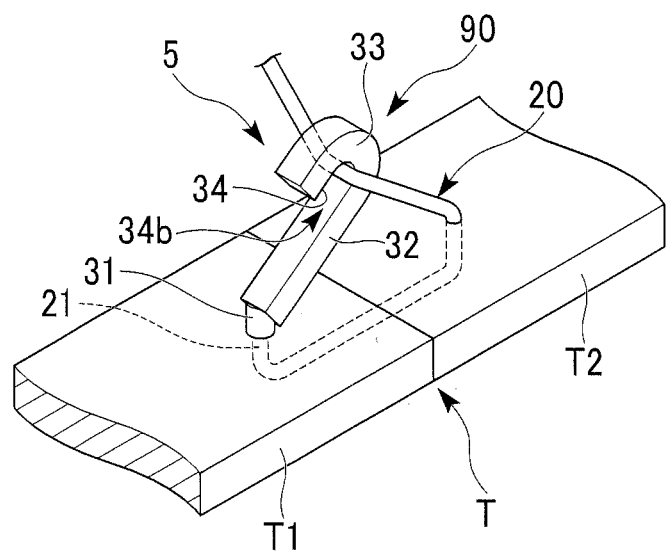
FIG. 23 is an explanatory view showing an operation of stitching tissues using the tissue ligation device according to the fifth embodiment of the present invention.

When the hook-like member 90 is brought into contact with the tissue T1, the curved portion 33 of the hook-like member 90, as shown in FIG. 23, is kept located above the tissue T1.

The suture thread 20 is engaged with a groove 34 of the hook-like member 90, and the suture needle 40 is pulled so as to move away from an end 21 of the suture thread 20.

The following operation is similar to the case of using the device 1, and a description thereof will be omitted here.

As described above, according to the device 5 of the present fifth embodiment, it is possible to have effects similar to those of the device 3 of the third embodiment.

Generally, an operator performs a procedure while observing the tissues from the side of moving away from the tissues T1 and T2. Since the linear part 32 in the device 5 extends in a direction inclined with respect to the Z axis, a location of an opening 34b can be easily ascertained by the operator.

In the present fifth embodiment, the direction in which the linear part 32 extends is not limited to the aforementioned direction. Thus, the linear part 32 may extend toward the side of moving away from the suture thread 20 with respect to the orthogonal plane S1 that is the XY plane. The plane on which the curved portion 33 is disposed is not particularly restricted.

Figure 24:
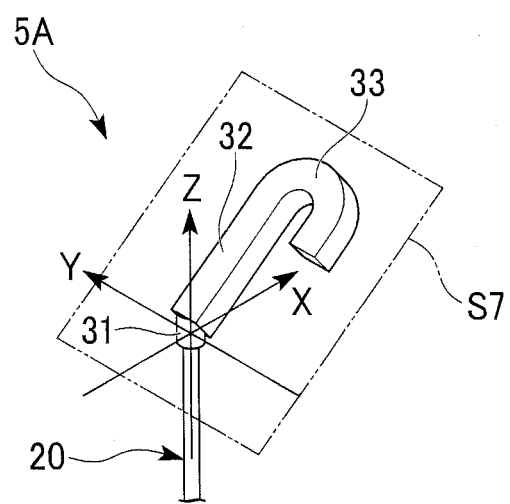
FIG. 24 is a perspective view of important parts of the tissue ligation device in a first modified example of the fifth embodiment of the present invention.

For a first modified example, as in a device 5A shown in FIG. 24, the linear part 32 and the curved portion 33 may be configured to be disposed together on a reference plane S7. The reference plane S7 is a plane that includes the Y axis and that passes through an area that is in the positive direction of the X axis and in the positive direction of the Z axis and an area that is in the negative direction of the X axis and in the negative direction of the Z axis.

Figure 25:
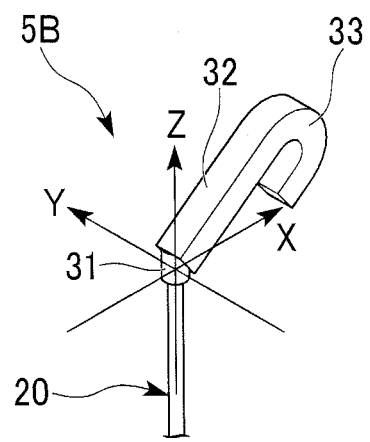
FIG. 25 is a perspective view of important parts of the tissue ligation device in a second modified example of the fifth embodiment of the present invention.

Further, as in a device 5B shown in FIG. 25 according to a second modified example, an end of the curved portion 33 which is located in the negative direction of the X axis may be configured so as to be connected to the linear part 32 in the device 5 of the present embodiment.

Even by the device 5A or 5B configured according to the first and second modified examples of the present fifth embodiment, it is possible to have effects similar to those of the device 5 of the present fifth embodiment.

Sixth Embodiment

Next, a sixth embodiment of the present invention will be described with reference to FIGS. 26 to 30. However, the same portions as in the aforementioned embodiments are assigned the same symbols, and a description thereof will be omitted here, and thus will be made regarding differences only.

Figure 26:
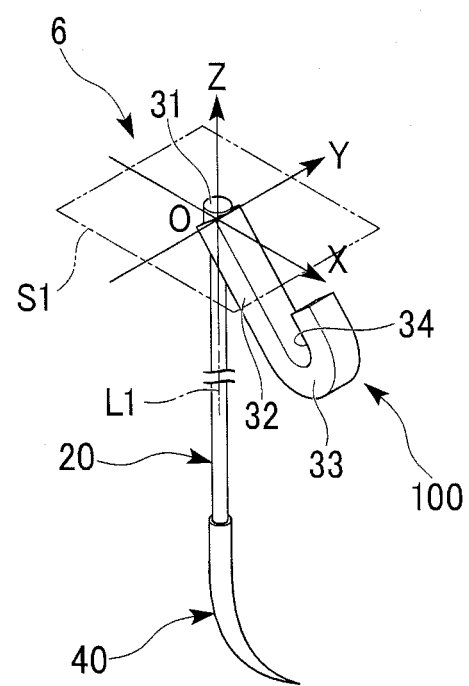
FIG. 26 is a perspective view of a tissue ligation device according to a sixth embodiment of the present invention.
Figure 27:
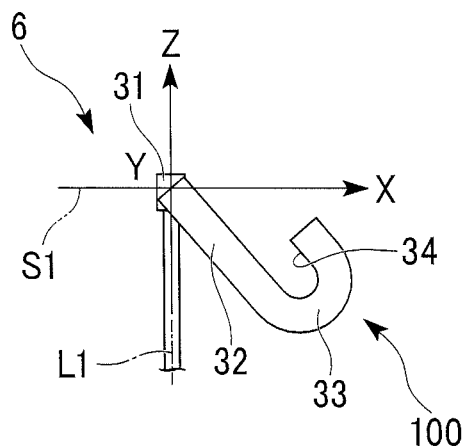
FIG. 27 is a side view of important parts of the tissue ligation device in the sixth embodiment of the present invention when viewed in the positive direction of the Y axis.

As shown in FIGS. 26 and 27, a device 6 of the present sixth embodiment includes a hook-like member 100 in place of the hook-like member 30 of the device 1 of the first embodiment.

The hook-like member 100 is different from the hook-like member 30 in terms of a direction in which a linear part 32 extends from a connecting portion 31. The linear part 32 extends from the connecting portion 31 in a direction between the positive direction of the X axis and the negative direction of the Z axis.

A curved portion 33 is curved on a ZX plane. An end of the curved portion 33 which is located in the negative direction of the X axis is connected to the linear part 32.

Next, an operation in use of the device 6 configured according to the present sixth embodiment will be described.

The suture thread 20 is threaded through tissues T1 and T2, and a suture needle 40 is pulled so as to move away from an opening T.

Figure 28:
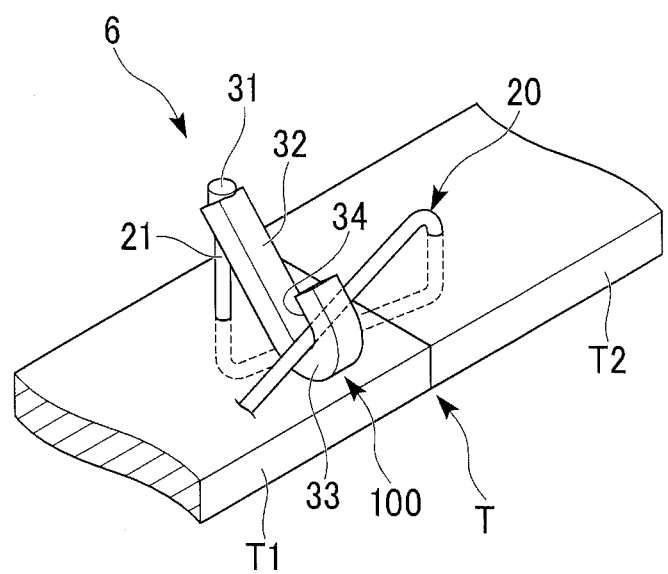
FIG. 28 is an explanatory view showing an operation of stitching tissues using the tissue ligation device according to the sixth embodiment of the present invention.

As shown in FIG. 28, after the hook-like member 100 is brought into contact with the tissue T1, the suture thread 20 is engaged with a groove 34 of the hook-like member 100, and is displaced so as to move away from an end 21.

Then, the suture thread 20 is kept tightened, and the curved portion 33 of the hook-like member 100 gets into the tissue T1.

In this state, the curved portion 33 is swaged, and the hook-like member 100 is fixed to the suture thread 20.

As described above, according to the device 6 of the present sixth embodiment, it is possible to have effects similar to those of the device 4 of the fourth embodiment.

In the present sixth embodiment, the direction in which the linear part 32 extends is not limited to the aforementioned direction. Thus, the linear part 32 may extend toward the suture thread 20 with respect to the orthogonal plane S1 that is the XY plane. The plane on which the curved portion 33 is disposed is not particularly limited.

Figure 29:
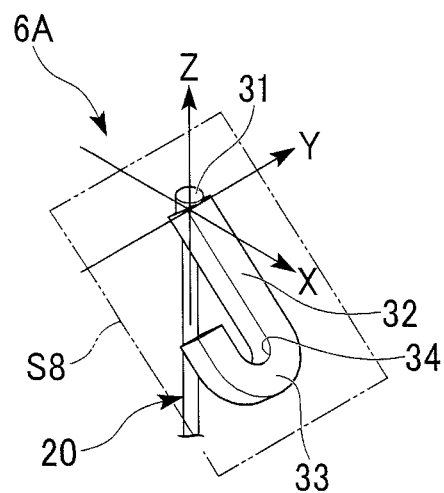
FIG. 29 is a perspective view of important parts of the tissue ligation device in a first modified example of the sixth embodiment of the present invention.

For a first modified example, as in a device 6A shown in FIG. 29, the linear part 32 and the curved portion 33 may be configured to be disposed together on a reference plane S8. The reference plane S8 is a plane that includes the Y axis and that passes through an area that is in the positive direction of the X axis and in the negative direction of the Z axis and an area that is in the negative direction of the X axis and in the positive direction of the Z axis.

Figure 30:
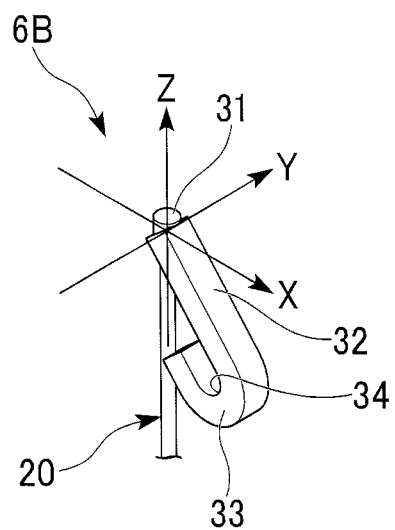
FIG. 30 is a perspective view of important parts of the tissue ligation device in a second modified example of the sixth embodiment of the present invention.

Further, as in a device 6B shown in FIG. 30 according to a second modified example, an end of the curved portion 33 which is located in the positive direction of the Z axis may be configured so as to be connected to the linear part 32 in the device 6 of the present embodiment.

Even by the device 6A or 6B configured according to the first and second modified examples of the present sixth embodiment, it is possible to have effects similar to those of the device 6 of the present sixth embodiment.

While the first to sixth embodiments of the present invention have been described in detail with reference to the drawings, specific configurations are not limited to these embodiments, and also include a change in the configuration without departing from the scope of the present invention. Furthermore, the configurations shown in each embodiment can be properly combined when used.

Hereinafter, modified examples of the hook-like member, the direction regulating part or the like will be described.

For example, in the first to sixth embodiments, the bent part is the curved portion 33 curved on the plane. However, a shape of the bent part is not limited to this shape. The bent part may be a flexural portion flexed on the plane.

Figure 31:
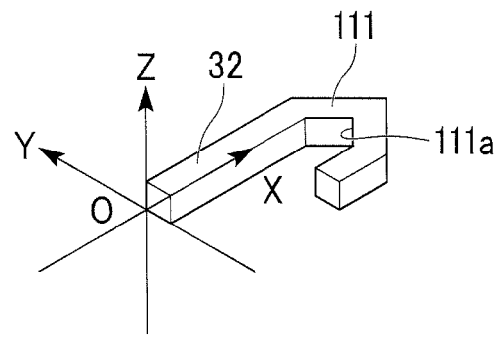
FIG. 31 is a perspective view of a hook-like member in a modified example of the embodiments of the present invention.

A flexural portion 111 shown in FIG. 31 is formed so as to be flexed on the XY plane. In this example, a bottom 111a of the flexural portion 111 is formed in a shape recessed approximately in a V shape when viewed from the top.

Figure 32:
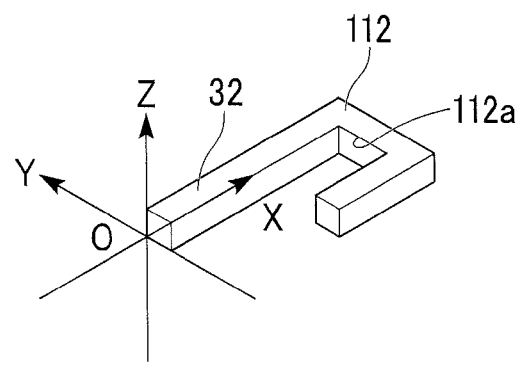
FIG. 32 is a perspective view of a hook-like member in a modified example of the embodiments of the present invention.

A flexural portion 112 shown in FIG. 32 is formed so as to be flexed on the XY plane. In this example, a bottom 112a of the flexural portion 112 is formed in a flat shape perpendicular to the X axis.

Figure 33:
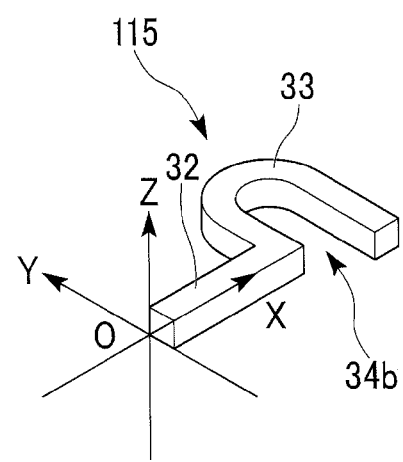
FIG. 33 is a perspective view of a hook-like member in a modified example of the embodiments of the present invention.

A hook-like member 115 shown in FIG. 33 is different from the hook-like member 30 in terms of a direction in which a curved portion 33 is connected to a linear part 32.

In the hook-like member 30, the opening 34b is formed so as to be directed in the negative direction of the X axis. However, in the hook-like member 115, the curved portion 33 is disposed on the XY plane, and simultaneously the opening 34b is formed so as to be directed in the negative direction of the Y axis.

Further, in the embodiments and modified examples, the bent part is formed so as to be curved or flexed on the plane. However, the bent part may be formed so as to be curved or flexed on a curved surface.

Figure 34A:
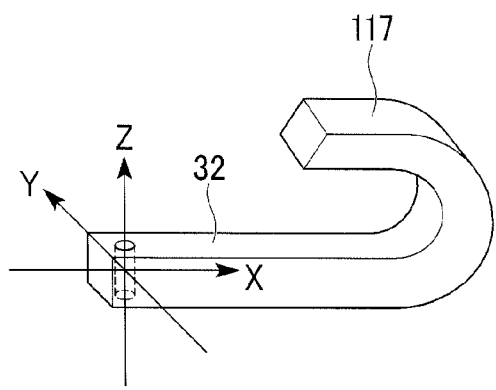
FIG. 34A is a perspective view of a hook-like member in a modified example of the embodiments of the present invention.
Figure 34B:
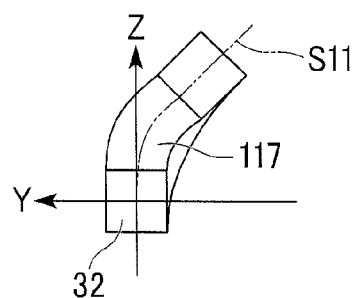
FIG. 34B is a front view of a hook-like member in a modified example of the embodiments of the present invention when viewed in the positive direction of the X axis.

For example, a curved portion 117 shown in FIGS. 34A and 34B is formed so as to be curved on a reference plane S11 that is curved from the XY plane in the positive direction of the Z axis.

Figure 35A:
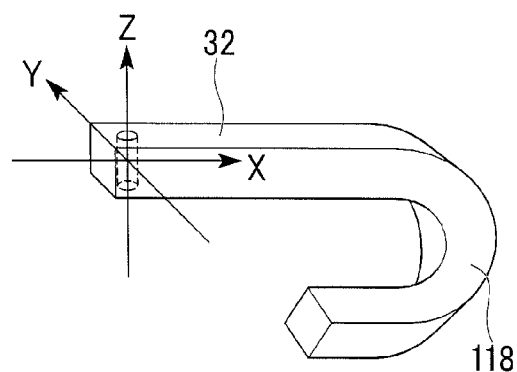
FIG. 35A is a perspective view of a hook-like member in a modified example of the embodiments of the present invention.
Figure 35B:
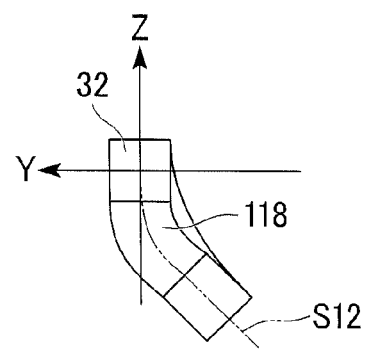
FIG. 35B is a front view of a hook-like member in a modified example of the embodiments of the present invention when viewed in the positive direction of the X axis.

Further, a curved portion 118 shown in FIGS. 35A and 35B is formed so as to be curved on a reference plane S12 that is curved from the XY plane in the negative direction of the Z axis.

In addition to the direction regulating part 51 used in the first to sixth embodiments, a variety of direction regulating parts may be used.

Figure 36:
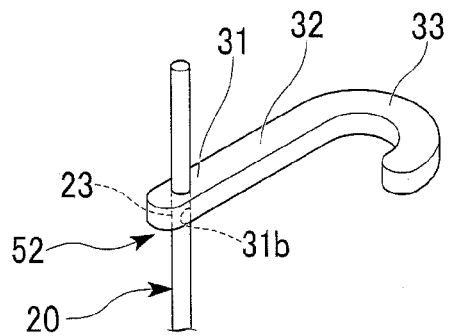
FIG. 36 is a perspective view of main parts of the tissue ligation device in a modified example of the embodiments of the present invention.

For example, as shown in FIG. 36, a direction regulating part 52 may be configured so that an intermediate part (suture thread-side connecting portion) 23 of the suture thread 20 is pressed into the through-hole 31b formed in the connecting portion 31.

Figure 37:
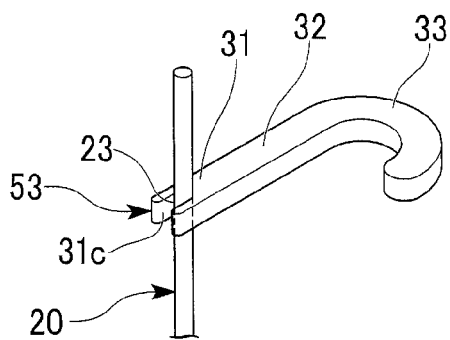
FIG. 37 is a perspective view of main parts of the tissue ligation device in a modified example of the embodiments of the present invention.

As shown in FIG. 37, a direction regulating part 53 may be configured so that the intermediate part 23 of the suture thread 20 is pressed into a notch 31c formed in the connecting portion 31.

Figure 38:
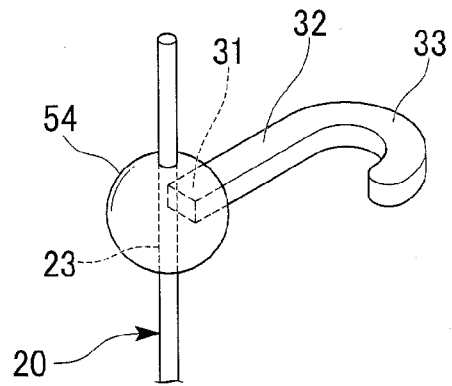
FIG. 38 is a perspective view of main parts of the tissue ligation device in a modified example of the embodiments of the present invention.

As shown in FIG. 38, the connecting portion 31 and the intermediate part 23 of the suture thread 20 may be fixed by an adhesive (direction regulating part) 54 formed of a resin. The examples of the direction regulating part 53 and the adhesive 54 are allowed to simplify the direction regulating part, because the suture thread 20 may not pass through the hole formed in the connecting portion 31.

Figure 39:
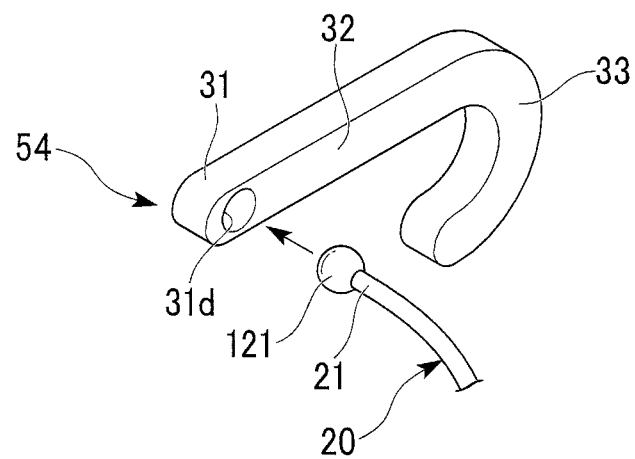
FIG. 39 is an exploded view of main parts of the tissue ligation device in a modified example of the embodiments of the present invention.

As shown in FIG. 39, a direction regulating part 54 may be configured so that a ball joint 121 provided at the end 21 of the suture thread 20 is disposed in the fixing hole 31d formed in the connecting portion 31 and then is fixed to the fixing hole 31d by a screw (not shown). In this example, the direction of the suture thread 20 can be easily adjusted to the connecting portion 31.

Figure 40:
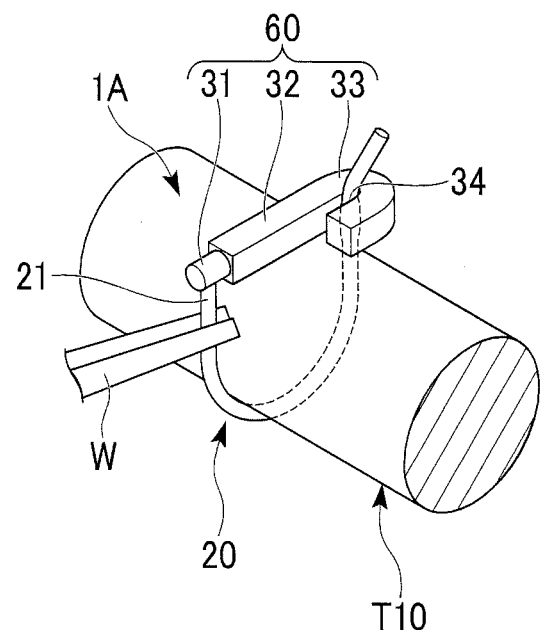
FIG. 40 is an explanatory view showing an operation of stitching tissues using the tissue ligation device in a modified example of the embodiments of the present invention.

Further, in the first to sixth embodiments, no suture needle 40 may be provided in the device. As this example, a case in which a blood vessel (tissue) T10 is stitched using a device 1A that is shown in FIG. 40 and configured so that no suture needle 40 is provided in the device 1 of the first embodiment will be described.

An operator grips the end 21 of the suture thread 20 with the grasping forceps W, and holds a position of the end 21 of the suture thread 20 in the vicinity of the blood vessel T10.

The operator grips the other end 22 of the suture thread 20 with another grasping forceps (not shown), guides the suture thread 20 around the blood vessel T10, and forms a loop. Then, the suture thread 20 is engaged with the groove 34 of the hook-like member 30.

The curved portion 33 is swaged by the grasping forceps, and thus the hook-like member 30 is fixed to the suture thread 20. The suture thread 20 is cut at the other end 22 side than the hook-like member 30. The procedure is terminated.

Further, in the first to sixth embodiments, the hook-like member has been described to be formed of the material that can undergo the plastic deformation. However, when the hook-like member is configured to be able to be fixed to the suture thread 20 by pressing the suture thread 20 into the groove 34, the hook-like member may be formed of a material such as a hyperelastic material that is subjected to only elastic deformation without plastic deformation.

In the first to sixth embodiments, the connecting portion 31 and the curved portion 33 have been described to be connected to the linear part 32 formed in the rod shape. However, the connecting portion 31 and the curved portion 33 may be configured so as to be connected to a member formed in a corrugated or zigzag shape, in place of the linear part 32.

Further, in the first to sixth embodiments, the direction regulating part is optional. This is because, if the hook-like member has the locking surface 34c, it is possible to lock the suture thread 20 on the hook-like member and to form the loop of the suture thread 20.

The linear part 32 and the curved portion 33 have been described to be formed in the rectangular cross-sectional shape by the plane perpendicular to the direction in which each extends. However, the cross-sectional shape is not limited to the rectangular cross-sectional shape, and thus may be a circular shape or an oval shape, and a polygonal shape other than the rectangular shape.

In the third to sixth embodiments, the operation of the device in use has been described taking the case in which, after the hook-like member is brought into contact with the tissue T1, the suture thread 20 is engaged with the groove 34 of the hook-like member by way of example. However, before the hook-like member is brought into contact with the tissue T1, the suture thread 20 may be engaged with the groove 34. Then, suture thread 20 may be tightened, and the hook-like member may be brought into contact with the tissue T1.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A tissue ligation device for ligating tissues, comprising:
a suture thread; and
a hook-like member having:
    a connecting portion opening for accepting a suture thread-side connecting portion of the suture thread;
    a groove whose inner wall has a locking surface disposed so as to face the suture thread-side connecting portion and allowed to be brought into contact with the suture thread, and
    a linear part extending linearly from the connecting portion opening,
wherein the suture thread-side connecting portion is an end of the suture thread,
the suture thread extends from the connecting portion opening towards an other end of the suture thread adapted to hold a needle; and
the groove includes a crimping portion for securing a portion of the suture in the groove, the crimping portion being open from a same side of the hook-like member as the connection portion opening.

2. The tissue ligation device according to claim 1, further comprising a direction regulating part that regulates a direction of the suture thread-side connecting portion with respect to the hook-like member.

3. The tissue ligation device according to claim 1, wherein the hook-like member includes a bent part, one end of which is connected to the linear part, and which is curved or flexed on a reference plane including the linear part, thereby providing the groove in which an opening is formed toward the connecting portion.

4. The tissue ligation device according to claim 1, further comprising the needle connected to the other end of the suture thread.

* * * * *